(12) United States Patent
Matsunobu (10) Patent No.: US 11,134,842 B2
(45) Date of Patent: Oct. 5, 2021

(54) OBSERVATION SYSTEM AND NON-TRANSITORY COMPUTER-READABLE MEDIUM STORING COMPUTER-READABLE INSTRUCTIONS

(71) Applicant: NIDEK CO., LTD., Gamagori (JP)

(72) Inventor: Go Matsunobu, Okazaki (JP)

(*) Notice: Subject to any disclaimer, the term of this patent is extended or adjusted under 35 U.S.C. 154(b) by 214 days.

(21) Appl. No.: 16/432,189

(22) Filed: Jun. 5, 2019

(65) Prior Publication Data

US 2019/0282091 A1 Sep. 19, 2019

Related U.S. Application Data

(63) Continuation of application No. PCT/JP2017/043260, filed on Dec. 1, 2017.

(30) Foreign Application Priority Data

Dec. 6, 2016 (JP) .............................. JP2016-236608

(51) Int. Cl.
 *A61B 3/14* (2006.01)
 *A61B 3/10* (2006.01)

(52) U.S. Cl.
 CPC .................. *A61B 3/14* (2013.01); *A61B 3/10* (2013.01); *A61B 3/102* (2013.01)

(58) Field of Classification Search
 CPC .. A61B 3/14; A61B 3/10; A61B 3/102; A61B 3/0025; A61B 3/113; A61B 3/0033;
(Continued)

(56) References Cited

U.S. PATENT DOCUMENTS

2003/0231393 A1* 12/2003 Yamamoto ........... G02B 27/646
                                                      359/557
2007/0070294 A1 3/2007 Kim
(Continued)

FOREIGN PATENT DOCUMENTS

JP 2007-534428 A 11/2007
JP 2011-200533 A 10/2011
(Continued)

OTHER PUBLICATIONS

Feb. 14, 2020 Office Action issued in Japanese Patent Application No. 2018-554970.
(Continued)

*Primary Examiner* — Mohammed A Hasan
(74) *Attorney, Agent, or Firm* — Oliff PLC (57) ABSTRACT

An observation system includes an observation optical system, an imaging device, an observation focus adjustment unit, a detector, and a processor. The observation optical system guides an observation luminous flux from a biological object being an observation target. The imaging device captures an observation image of the biological object, by receiving the observation luminous flux guided by the observation optical system. The observation focus adjustment unit adjusts a focus of the observation optical system. The detector detects at least one of a direction of a line of sight of the user, voice generated by the user, or a gesture of the user. The processor causes the observation image to be displayed on a display, and adjusts a focus of a target region concentrated on by the user in the observation image, by driving the observation focus adjustment unit based on a detection result by the detector.

10 Claims, 6 Drawing Sheets

(58) Field of Classification Search
CPC ...... A61B 3/13; G02B 21/0012; G02B 21/22; G02B 21/241
See application file for complete search history.

(56) References Cited

U.S. PATENT DOCUMENTS

2015/0335479 A1    11/2015  Shibata et al.
2018/0035887 A1*  2/2018  Nakanishi .............. A61B 90/20

FOREIGN PATENT DOCUMENTS

| | | |
|---|---|---|
| JP | 2014-207976 A | 11/2014 |
| JP | 2015-163092 A | 9/2015 |
| JP | 2016-30029 A | 3/2016 |

OTHER PUBLICATIONS

Sep. 14, 2020 Office Action issued in Japanese Patent Application No. 2018-554970.
Feb. 27, 2018 International Search Report issued in International Patent Application PCT/JP2017/043260.
Feb. 27, 2018 Written Opinion issued in International Patent Application PCT/JP2017/043260.
Jun. 23, 2021 Office Action issued in Japanese Patent Application No. 2018-554970.

* cited by examiner

FIG. 6

OBSERVATION SYSTEM AND NON-TRANSITORY COMPUTER-READABLE MEDIUM STORING COMPUTER-READABLE INSTRUCTIONS

CROSS-REFERENCE TO RELATED APPLICATION

This application is a continuation application of International Application No. PCT/JP2017/043260, filed Dec. 1, 2017, which claims priority from Japanese Patent Application No. 2016-236608, filed Dec. 6, 2016. The disclosure of the foregoing applications is hereby incorporated by reference in their entirety.

BACKGROUND

The present disclosure relates to an observation system used to observe a biological object, and a non-transitory computer-readable medium storing computer-readable instructions.

Various systems are known that allow a user (such as a surgeon) to observe a biological object when performing an operation, an examination, a diagnosis, or the like. For example, in a known ophthalmic surgical microscope, an observation optical system is provided with an observation optical path for the user's right eye and an observation optical path for the user's left eye. By using both eyes to observe a patient's eye, which is an observation object, through left and right eyepieces, the user stereoscopically views the patient's eye.

SUMMARY

In the observation system, when a position that the user is paying particular attention to is frequently changed, or the like, it may be desirable that the focus of the position to which attention is paid is rapidly and finely brought into focus. In the observation system that allows the user to observe the biological object through the eyepieces, focusing is performed by operating an operation switch or the like, and fine focusing is performed by the eyes of the user. Thus, the fine focusing is performed even without the user finely operating the operation switch or the like. However, when an image of the biological object is captured and caused to be displayed on a display in order for the user to observe the biological object, it may be desirable that the fine focusing is performed in the observation system. In this case, in a conventional observation system, it is necessary for the user to operate the operation switch or the like and perform the fine focusing, which may in some cases obstruct the progress of a surgical operation or the like.

Embodiments of the broad principles derived herein provide an observation system capable of enabling an observation image of a biological object displayed on a display to be appropriately focused, and a non-transitory computer-readable medium storing computer-readable instructions.

Embodiments provide an observation system that includes: an observation optical system guiding an observation luminous flux from a biological object being an observation target observed by a user; an imaging device capturing an observation image of the biological object, by receiving the observation luminous flux guided by the observation optical system; an observation focus adjustment unit provided on an optical path of the observation luminous flux in the observation optical system, the observation focus adjustment unit adjusting a focus of the observation optical system; a detector detecting at least one of a direction of a line of sight of the user, voice generated by the user, or a gesture of the user; and a processor controlling an operation of the observation system. The processor causes the observation image captured by the imaging device to be displayed on a display, and adjusts a focus of a target region concentrated on by the user in the observation image, by driving the observation focus adjustment unit based on a detection result by the detector.

Embodiments further provide a non-transitory computer-readable medium storing computer-readable instructions that, when executed by a processor of a control unit controlling an observation system, cause the control unit to perform processes including: causing an observation image captured by an imaging device to be displayed on a display, the observation system including an observation optical system and the imaging device, the observation optical system guiding an observation luminous flux from a biological object, and the imaging device capturing the observation image of the biological object, by receiving the observation luminous flux guided by the observation optical system; and adjusting a focus of a target region concentrated on by the user in the observation image, by driving an observation focus adjustment unit based on a detection result by a detector, the observation system further including the observation focus adjustment unit and the detector, the observation focus adjustment unit being provided on an optical path of the observation luminous flux in the observation optical system, the observation focus adjustment unit adjusting a focus of the observation optical system, and the detector detecting at least one of a direction of a line of sight of the user, voice generated by the user, or a gesture of the user.

DETAILED DESCRIPTION

An observation system exemplified in the present disclosure includes an observation optical system, an imaging device, an observation focus adjustment unit, a detector, and a processor. The observation optical system guides an observation luminous flux from a biological object being an observation target. The imaging device captures an observation image of the biological object, by receiving the observation luminous flux guided by the observation optical system. The observation focus adjustment unit is provided on an optical path of the observation luminous flux in the observation optical system. The observation focus adjustment unit adjusts a focus of the observation optical system (hereinafter sometimes referred to as an "observation focus"). The detector detects at least one of a direction of a line of sight of the user, voice generated by the user, or a gesture of the user. The processor causes the observation image captured by the imaging device to be displayed on a display. Further, the processor adjusts a focus of a target region concentrated on by the user in the observation image, by driving the observation focus adjustment unit based on a detection result by the detector.

In this case, the focus of the target region can be appropriately adjusted even without the user operating an operation unit using the user's hand or foot. Thus, the user can appropriately observe the biological object.

The observation optical system may guide an observation luminous flux for a right eye and an observation luminous flux for a left eye from the biological object to the imaging device. The processor may cause a stereoscopic image to be displayed on a stereoscopic image display, based on an imaging signal for the right eye and an imaging signal for the left eye that are issued by the imaging device. Specifically, the observation system may be a three-dimensional digital microscope that causes the stereoscopic image of the observation target to be displayed on the stereoscopic image display. In this case, even when the user is holding a surgical instrument or the like, the user can easily and appropriately observe a position on which the user wishes to concentrate.

At least a part of the technology exemplified in the present disclosure may be applied to a system or a device other than the three-dimensional digital microscope. For example, the technology exemplified in the present disclosure may be applied to a device that performs various measurements, image capture, or the like while capturing an image of a biological object and displaying the image on a display (for example, among ophthalmological devices, this includes a fundus camera, an eye refractivity measuring device, a corneal shape measuring device, a tomographic image capturing device, and the like).

The detector may include a camera. The detector may detect the gesture by a face of the user. In this case, the user can appropriately observe the biological object by moving the user's face.

The processor may set the target region on the observation image captured by the imaging device, based on the detection result by the detector. The processor may acquire a focus state of the observation optical system, and may adjust the focus of the target region in the observation image, by driving the observation focus adjustment unit based on an acquisition result. In this case, even when the position to be concentrated on by the user changes, the user can appropriately observe the biological object.

The detector may include a line of sight direction detector that detects the direction of the line of sight of the user. The processor may set the target region to a region, of the observation image displayed on the display, that is positioned in the direction of the line of sight detected by the line of sight direction detector. In this case, the position on which the user actually concentrates can be automatically focused. Thus, the biological object can be appropriately observed by the user even without the user inputting various commands.

Various methods may be applied as the method to detect the direction of the line of sight. For example, the direction of the line of sight may be detected by capturing an image of the inner corner of the eye and the iris of the user using a visible light camera, and detecting a positional relationship between the inner corner of the eye and the iris by processing the captured image. In this case, for example, if the iris is at a distance from the inner corner of the eye, it is detected that the user is looking to the side of the outer corner of the eye. The direction of the line of sight may be detected by capturing an image of the pupil and the corneal reflex bright spot of the user using an infrared camera, and detecting a positional relationship between the pupil and the corneal reflex bright spot by processing the captured image. In this case, for example, when the pupil is further to the outer corner side of the eye than the corneal reflex bright spot, it is detected that the user is looking to the side of the outer corner of the eye.

The detector need not necessarily include the line of sight direction detector. For example, the detector may include a voice detector that detects voice generated by the user. The processor may set the target region in accordance with the voice detected by the voice detector. In this case, the position concentrated on by the user is focused even without the user operating an operation switch or the like. The detector may include a gesture detector that detects a gesture of the user. The processor may set the target region in accordance with the gesture detected by the gesture detector. In this case, since there is no need for the user to touch the operation switch or the like, the hands and so on of the user remain clean.

A plurality of modes may be provided, including a mode that performs automatic focus adjustment of the target region based on an acquisition result of an observation focus state, and a mode that stops the automatic focus adjustment. The processor may receive an input of a selection command to select one of the plurality of modes, and may control an operation of the automatic focus adjustment in accordance with the selected mode. In this case, the user can select the desired mode and can appropriately observe the biological object in accordance with various situations.

An execution mode may include a signal input execution mode in which the automatic focus adjustment is performed when a trigger signal is input. When the signal input execution mode is selected, by using an input of the trigger signal as a trigger, the processor may set the target region and perform the focus adjustment of the target region. In this case, the user can focus the target region at a desired timing by inputting the trigger signal.

The execution mode may include a constant execution mode in which the automatic focus adjustment is constantly performed. When the constant execution mode is selected, the processor may constantly or intermittently performs setting the target region and adjusting the focus of the target region. In this case, the focus of the target region can be constantly appropriately adjusted.

The processor may acquire the focus state of the observation optical system based on a signal inside the set target region, of signals from the imaging device. In this case, the observation focus state can be appropriately acquired to focus the target region, using the imaging device used to capture the observation image. Thus, the observation system can appropriately acquire the observation focus state while suppressing an increase in a dedicated configuration to acquire the observation focus state.

Various methods may be applied as the method for acquiring the observation focus state on the basis of the signal from the imaging device. For example, the processor may acquire the observation focus state using a contrast detection method. In this case, the processor may acquire the observation focus state by analyzing the image inside the target region of the observation image captured by the imaging device while changing the observation focus, and causing a position at which the contrast of the image inside the target region is high to be the position at which the observation focus is in focus.

A method other than the contrast detection method may be used. For example, the processor may acquire the observation focus state using an image surface phase difference detection method. In this case, a phase difference pixel formed in an asymmetrical shape in the left-right direction to detect an image phase difference (parallax) is incorporated into part of the pixels of the imaging device. The processor calculates the phase difference based on a signal obtained by selectively receiving light incident from one of a left or a right direction, using the phase difference pixel. The processor may acquire the focus state by causing a position at which the phase difference is small to be the position at which the observation focus is in focus.

A phase difference detection method in which a phase difference detection sensor other than the imaging device is used may be applied. In this case, a surgical microscope may include a separator lens that creates two images from the observation luminous flux, and the phase difference detection sensor for detecting the phase difference (parallax) from the two images, for example. The processor may calculate the phase difference based on a signal obtained using the phase difference detection sensor, and may acquire the observation focus state by causing the position at which the phase difference is small to be the position at which the observation focus is in focus.

For example, the observation focus state may be acquired using an astigmatism method, a knife edge method, a Foucault method, a critical angle method, or the like. The astigmatism method is a method in which the focus state is detected using an astigmatism that arises due to a difference between focal positions of a cylindrical lens and an objective lens. The knife edge method is a method in which a wall (knife edge) that blocks light of half an optical path is provided on an objective lens focal point between the objective lens and a dual cell photodiode, and the focus state is detected with an amount of light incident on the dual cell photodiode. The Foucault method is a method in which the focus state is detected by using two dual cell photodiodes to detect a change in an optical path that occur as a result of a relationship between a position of a condensing point by an objective lens and a prism surface position. The critical angle method is a method in which the focus state is detected by using a dual cell photodiode to detect a change in a ratio between light reflectance and transmittance, using a critical angle prism.

A hybrid method may be used in which a plurality of the detection methods are combined. For example, a hybrid detection method in which the contrast detection method and the image surface phase difference detection method are combined, or the like, may be adopted. When the hybrid detection method is used, even if an error occurs in one of the detection methods, the focus state can be appropriately detected by the other detection method.

The processor may receive an input of an offset amount (a deviation amount) of a focus position desired by the user, with respect to a focus position of the observation focus that is adjusted on the basis of an acquisition result of the observation focus state. The processor may bring the observation focus into focus at a position that is deviated, by the input offset amount, from the focus position that is based on the acquisition result of the observation focus state. In this case, the position is brought into focus that is deviated by the desired amount with respect to a normal focus position focused by the automatic focus. Thus, the user can more appropriately observe the biological object.

The observation system may include an OCT unit that acquires an OCT signal. The OCT unit may include an OCT light source, a light splitter, a photodetection element, and an optical path length difference adjustment unit. The OCT light source may emit OCT light. The light splitter may split a luminous flux emitted from the OCT light source into a measurement luminous flux and a reference luminous flux. The photodetection element may receive interference light obtained by synthesizing the reference luminous flux and the measurement luminous flux reflected by the biological object. The optical path length difference adjustment unit may be provided on at least one of an optical path of the measurement luminous flux or an optical path of the reference luminous flux, and may adjust an optical path length difference between the measurement luminous flux and the reference luminous flux. The processor may set a position at which the OCT unit causes the measurement luminous flux to perform scanning, based on the detection result by the detector, and may drive the optical path length difference adjustment unit in accordance with a change in a focus state of the target region.

In this case, a position at which the OCT signal is acquired is set on the basis of a position concentrated on by the user. Thus, a tomographic image or the like of the position concentrated on by the user can be appropriately acquired. Further, in addition to the focus of the target region being appropriately adjusted, the optical path length difference of the OCT unit can be appropriately adjusted. Thus, the OCT signal can be more appropriately acquired. More specifically, when only automatic optical path length (OPL) adjustment is performed that searches for a position at which the tomographic image is acquired while changing the optical path length difference, it is necessary for the processor to search over a wide range while significantly changing the optical path length difference. In contrast, the observation system according to the present disclosure can adjust the optical path length difference of the OCT unit in concert with the adjustment of the observation focus that can be adjusted in a shorter length of time than the automatic optical path length adjustment, for example. Thus, the adjustment of the OCT light can be rapidly and appropriately performed.

A specific method for driving the optical path length difference adjustment unit in accordance with the change in the observation focus state in the target region may be selected as appropriate. For example, the processor may calculate a change amount $\Delta Z$ of a position to be observed on the basis of a drive amount of the observation focus adjustment unit, and may determine a drive amount of the optical path length difference adjustment unit on the basis of the calculated $\Delta Z$. Alternatively, a ratio between a movement amount of the observation focus corresponding to the drive amount of the observation focus adjustment unit and the change amount of the optical path length difference corresponding to the drive amount of the optical path length difference adjustment unit may be used. In this case, the processor may determine the drive amount of the optical path length difference adjustment unit in accordance with the drive amount of the observation focus adjustment unit and the above-described ratio. The processor may detect a deviation of the current observation focus with respect to an appropriate observation focus, and may determine the drive amount of the optical path length difference adjustment unit on the basis of the detected deviation of the observation focus. In this case also, the adjustment of the optical path length difference can be appropriately performed in accordance with the change in the observation focus state. The processor may drive the optical path length difference adjustment unit after driving the observation focus adjustment unit. The processor may simultaneously drive the observation focus adjustment unit and the optical path length difference adjustment unit in concert with each other.

The observation system may be a single device in which the surgical microscope and the OCT unit are integrated. The observation system may be a system that includes the surgical microscope, and an OCT device that is a separate device from the surgical microscope. The processor that controls the adjustment of the OCT light may be a processor provided in the OCT unit, or may be a processor provided in the surgical microscope. A processor of a personal computer or the like that is connected to each of the surgical microscope and the OCT unit may control the adjustment of the OCT light. Processors provided in each of a plurality of devices (the surgical microscope and the OCT device, for example) may control the adjustment of the OCT light in collaboration with each other.

The processor may analyze the OCT signal acquired via a photodetection element, and may drive the optical path length difference adjustment unit on the basis of the change in the observation focus state of the target region and an analysis result of the OCT signal. In this case, the optical path length difference adjustment unit is driven while also taking into account the analysis result of the OCT signal that is actually acquired. Thus, the adjustment of the optical path length difference can be more appropriately performed.

In this case, a specific method for controlling the optical path length difference adjustment unit may be selected as appropriate. For example, after driving the optical path length difference adjustment unit to a first position on the basis of the drive amount of the observation focus adjustment unit, the processor may drive the optical path length difference adjustment unit on the basis of the analysis result of the OCT signal (to a position at which a level of the OCT signal is equal to or greater than a threshold value, for example). The processor may determine the position at which to stop the driving by referring to the analysis result of the OCT signal, while driving the optical path length difference adjustment unit toward the first position on the basis of the drive amount of the observation focus adjustment unit. The optical path length difference adjustment unit may be driven without using the analysis result of the OCT signal.

When a change in the target region or the like has occurred, there is a case in which it is more preferable to adjust the focus of the OCT measurement luminous flux (hereinafter referred to as an "OCT focus"). The processor may drive an OCT focus adjustment unit in accordance with the change in the observation focus state of the target region. In this case, the OCT focus can be rapidly and appropriately adjusted along with the optical path length difference.

The processor may drive the OCT focus adjustment unit based on the change in the observation focus state of the target region and the analysis result of the OCT signal. In this case, the OCT focus adjustment unit is driven while also taking into account the analysis result of the OCT signal that is actually acquired. Thus, the adjustment of the OCT focus can be more appropriately performed. A specific method for controlling the OCT focus adjustment unit may be selected as appropriate, similarly to the specific method for controlling the optical path length difference adjustment unit.

The scanning position and the target region may be independent of each other, without setting the scanning position of the OCT light in the target region. The adjustment of the OCT light need not necessarily be performed in concert with the change in the observation focus of the target region. The observation system may only perform processing to adjust the focus of the target region in the observation image, without being provided with the OCT unit.

Technologies exemplified in the present disclosure may be performed in combination, as appropriate. For example, the observation system may set the scanning position of the OCT light on the basis of a detection result of voice generated by the user, without performing the automatic focus adjustment of the target region on the basis of the acquisition result of the observation focus state. In this case, the observation system may be expressed as described below. The observation system comprising: an OCT light source; a light splitter splitting a luminous flux emitted from the OCT light source into a measurement luminous flux and a reference luminous flux; a photodetection element receiving interference light obtained by synthesizing the reference luminous flux and the measurement luminous flux reflected by the biological object; a scanning unit causing the measurement luminous flux to scan; a voice detector detecting voice generated by a user; and a setting unit setting a scanning position of the measurement luminous flux in accordance with a detection result of the voice detected by the voice detector.

Hereinafter, an exemplary embodiment of the present disclosure will be described with reference to the drawings. In the present embodiment, an observation system 100 for performing stereoscopic viewing and the like of a patient's eye during ophthalmic surgery is exemplified. However, at least a portion of the technology exemplified in the present embodiment may be applied to an observation system used for a purpose other than ophthalmology. Further, in the present embodiment, the observation system 100 is exemplified in which an observation image captured by a surgical microscope 1 is stereoscopically displayed on a display 67. However, at least a portion of the technology exemplified in the present embodiment may be applied to an observation stem that allows a user to observe a biological object using another method.

Figure 1:
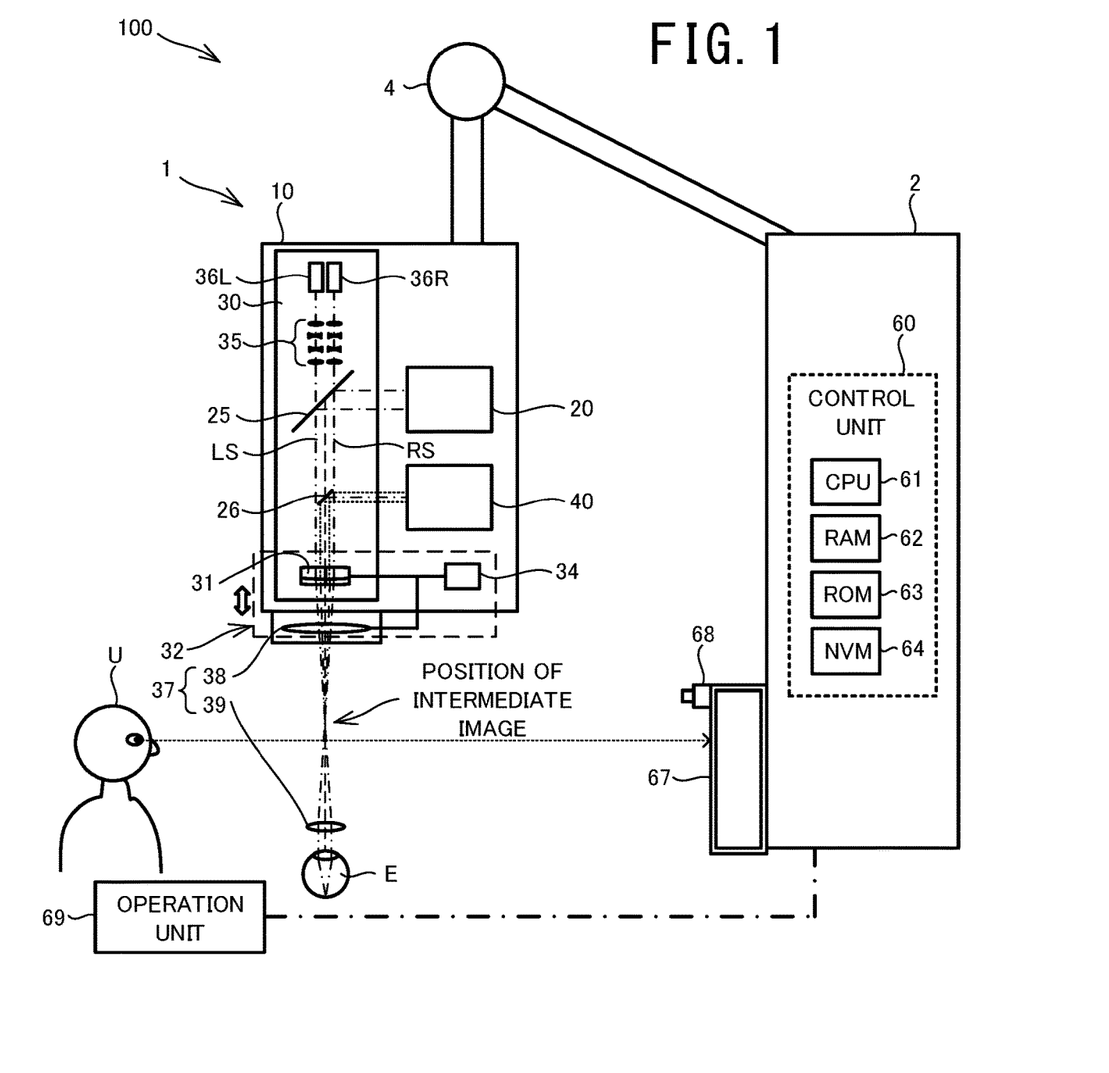
FIG. 1 is a view showing an overall configuration of an observation system 100.

As illustrated in FIG. 1, the observation system 100 of the present embodiment includes a surgical microscope 1, an OCT unit 40, and a control unit 60. In the following description, a direction parallel to observation luminous fluxes RS and LS of the surgical microscope 1 is referred to as a Z direction, and a direction that intersects the Z direction is referred to as an XY direction.

The surgical microscope 1 will be explained. As shown in FIG. 1, the surgical microscope 1 of the embodiment includes a base unit 2, an arm unit 4, and an observation device 10. The base unit 2 is a portion that serves as a base of the surgical microscope 1. In this embodiment, a control unit 60, which is described below, is built in the base unit 2. The arm unit 4 has at least one joint, and movably supports the observation device 10.

The observation device 10 includes an illumination optical system 20, a beam splitter 25, a reflection mirror 26, and an observation optical system 30. The illumination optical system 20 emits illumination light that illuminates a biological object (a patient's eye E in this embodiment) that is an observation object. The illumination optical system 20 is capable of emitting illumination light coaxial with the optical axis of the observation luminous flux RS for the right eye in the observation optical system 30 and illumination light coaxial with the optical axis of the observation luminous flux LS for the left eye in the observation optical system 30. However, the illumination light may be illumination light irradiated toward the observation object from an angle that differs from the optical axis of the observation luminous fluxes RS and LS. The observation luminous fluxes RS and LS in this embodiment refer to luminous fluxes guided by the observation optical system 30 to produce light to be observed by a user U, of the luminous fluxes from the observation object (the luminous fluxes of the illumination light reflected by the observation object, for example).

The beam splitter 25 is an example of an optical axis coupling element that makes the optical axis of the illumination light emitted by the illumination optical system 20 and the optical axes of the observation luminous fluxes RS and LS in the observation optical system 30 coaxial. The beam splitter 25 illustrated in FIG. 1 makes the optical axis of the illumination light and the optical axes of the observation luminous fluxes RS and LS coaxial by reflecting at least a portion of the illumination light emitted from the illumination optical system 20 and transmitting at least a portion of the observation luminous fluxes RS and LS from the observation object. The illumination light reflected by the beam splitter 25 travels along the same optical path as part of the optical path of the observation luminous fluxes RS and LS, in a direction opposite to the direction in which the observation luminous fluxes RS and LS travel, and is irradiated on the observation object.

The reflection mirror 26 reflects a measurement luminous flux for measuring an OCT signal emitted by the OCT unit 40 (to be described in detail below) toward the biological object. The reflection mirror 26 illustrated in FIG. 1 is provided in a position in which there is no interference with the observation luminous fluxes RS and LS and with illumination light (in the present embodiment, a position between the two observation luminous fluxes RS and LS). In FIG. 1, the reflection mirror 26 is provided between the beam splitter 25 and an observation focus adjustment unit 32 (to be described below). However, the position of the reflection mirror 26 may be appropriately changed in accordance with a position of the OCT unit 40 or the like.

The observation optical system 30 guides the observation luminous flux from the observation object to allow the user to observe (stereoscopically view, in this embodiment) the observation object. The surgical microscope 1 in this embodiment causes a display (a stereoscopic image display in this embodiment) 67 to display an observation image to be observed with the right eye of the user U and an observation image to be observed with the left eye of the user U (that is, causes the display 67 to display left and right microscopic images). The surgical microscope 1 can thus allow the user U to stereoscopically view the observation object. Therefore, the observation optical system 30 guides the right eye observation luminous flux RS from the observation object to a right eye imaging device 36R, and guides the left eye observation luminous flux LS from the observation object to a left eye imaging device 36L. The control unit 60 controls the image display of the display 67 on the basis of image signals from the two imaging devices 36R and 36L. Any of various kinds of devices, such as a three-dimensional display, a stereo viewer, and a head mounted display, for example, may be used for the display to cause stereoscopic vision of the observation object. There is no need to separately provide the right eye imaging device 36R, to which the right eye observation luminous flux RS is guided, and the left eye imaging device 36L, to which the left eye observation luminous flux LS is guided. For example, an area to which the right eye observation luminous flux RS is guided and an area to which the left eye observation luminous flux LS is guided may be provided in an imaging area of a single imaging device.

The user U may observe the biological object when a wide angle observation unit 37 is used. The wide angle observation unit 37 is used to widen an observation angle of view of the ocular fundus of the patient's eye E. For example, the user U may use the wide angle observation unit 37 when observing the ocular fundus of the patient's eye E. When observing the anterior ocular segment of the patient's eye E, the user U may remove the wide angle observation unit 37. In this way, the user U can perform an appropriate observation in accordance with a portion of the patient's eye E. The wide angle observation unit 37 of the present embodiment includes a reducing lens 38, which is arranged on the observation optical system 30 side, and a front lens 39, which is arranged on the patient's eye E side.

The observation optical system 30 includes an objective lens 31, the observation focus adjustment unit 32, a zoom lens group 35, and the imaging devices 36R and 36L described above. The observation focus adjustment unit 32 is provided on optical paths of the observation luminous fluxes RS and LS. The observation focus adjustment unit 32 can adjust the focus of the observation optical system 30. The zoom lens group 35 can change an image capture magnification of an image of the biological object captured by the imaging devices 36R and 36L. In the present embodiment, the image capture magnification is changed by at least one of the lenses in the zoom lens group 35 being moved in a direction that is along the observation luminous fluxes RS and LS.

As an example, the observation focus adjustment unit 32 of the present embodiment is provided with the objective lens 31, which is a positive lens of combined lenses, and an observation focus adjustment motor 34. Further, when the wide angle observation unit 37 is used, the reducing lens (positive lens) 38 of the wide angle observation unit 37 is also included in the observation focus adjustment unit 32. The observation focus adjustment motor 34 moves the objective lens 31 (the objective lens 31 and the reducing lens 38 when the wide angle observation unit 37 is used) in a direction that is along the observation luminous fluxes RS and LS. As a result, the focus of the observation optical system 30 (hereinafter referred to as an "observation focus") is changed. In the present embodiment, as the observation focus adjustment motor 34, a motor that moves the objective lens 31 and a motor that moves the reducing lens 38 are separately provided. Thus, both the objective lens 31 and the reducing lens 38, which is arranged on the outside of a lens barrel of the objective lens 31, are appropriately moved. However, the objective lens 31 and the reducing lens 38 may be moved by a single motor.

The configuration of the observation focus adjustment unit may be changed. For example, the observation focus adjustment unit may adjust the observation focus by moving at least one of the lenses in the zoom lens group 35 in a direction that is along the observation luminous fluxes RS and LS. In this case, in the example shown in FIG. 1, for example, at least one of the lenses in the zoom lens group 35 is, of the lenses arranged in order of a positive lens, a negative lens, a negative lens, and a positive lens from an upstream side on the optical path, the positive lens on the most upstream side. Further, the observation focus adjustment unit may include a negative lens 33 (see FIG. 9) that is located further to the imaging devices 36R and 36L side on the optical path than the objective lens 31. In this case, the observation focus adjustment unit may adjust the observation focus by using the observation focus adjustment motor 34 to move the negative lens 33 in a direction that is along the observation luminous fluxes RS and LS.

The observation optical system 30 may include a configuration for allowing the user U to stereoscopically view the observation object by looking through eyepieces. In this case, the observation optical system 30 may guide the right eye observation luminous flux RS to an eyepiece for the right eye of the user U and guide the left eye observation luminous flux LS to an eyepiece for the left eye of the user U.

The OCT unit 40 will be described. The OCT unit 40 uses the principle of optical coherence tomography (OCT) to acquire an OCT signal (an OCT tomographic image in the present embodiment). In the present embodiment, the OCT unit 40 is incorporated in the observation device 10 of the surgical microscope 1. In other words, in the present embodiment, the surgical microscope 1 and the OCT unit 40 are integrated. However, the surgical microscope 1 and the OCT unit 40 may be separate devices in the observation system 100.

Figure 2:
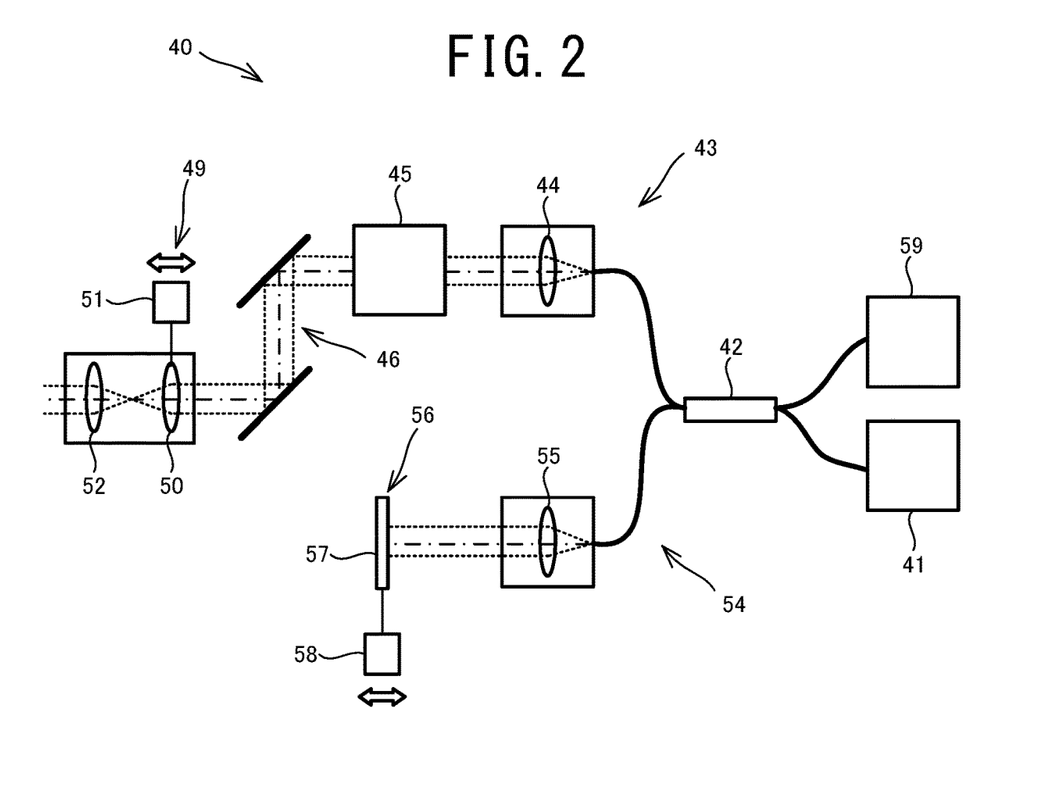
FIG. 2 is a view showing an overall configuration of an OCT unit 40.

The configuration of an optical system of the OCT unit 40 will be described with reference to FIG. 2. The OCT unit 40 includes an OCT light source 41, a coupler (light splitter) 42, a measurement optical system 43, a reference optical system 54, and a photodetection element (detector) 59. The OCT light source 41 emits light (OCT light) to acquire the OCT signal. The coupler 42 splits the luminous flux emitted from the OCT light source 41 into the measurement luminous flux and a reference luminous flux. Further, the coupler 42 of the present embodiment synthesizes the measurement luminous flux reflected by the biological object and the reference luminous flux generated by the reference optical system 54, and causes the synthesized light to be received by the photodetection element 59.

The measurement optical system 43 guides the measurement luminous flux split by the coupler 42 to the biological object (the patient's eye E), and returns the measurement luminous flux reflected by the biological object to the coupler 42. In the present embodiment, the measurement optical system 43 includes a collimator lens 44, an NA adjustment unit 45, an optical scanner 46, a lens 50, and a lens 52, in that order from the upstream side (the OCT light source 41 side) of the optical path. The collimator lens 44 causes the measurement luminous flux that has been split by the coupler 42 and has passed through a fiber to be a parallel luminous flux.

The NA adjustment unit 45 changes a beam diameter of the measurement luminous flux injected as the parallel luminous flux from the collimator lens 44. The NA adjustment unit 45 can thus adjust a numerical aperture NA of the measurement luminous flux concentrated toward the biological object. As an example, a known afocal zoom system is adopted in the NA adjustment unit 45 of the present embodiment. The control unit 60 controls the drive of a motor (not illustrated) provided in the NA adjustment unit 45 to move a lens provided in the NA adjustment unit 45 in an optical axis direction, thus changing the beam diameter. As a result, the numerical aperture NA of the measurement luminous flux concentrated toward the biological object is adjusted, and a horizontal resolution capacity and a focal depth at the time of acquiring the OCT signal are adjusted.

The optical scanner 46 causes the measurement luminous flux to scan in a two-dimensional direction as a result of being driven by a drive unit (not illustrated). As a result, an acquisition position of the OCT signal on the biological object is determined. The optical scanner 46 of the present embodiment is provided in a position substantially conjugate to the pupil of the patient's eye E. Further, in the present embodiment, two galvanometer mirrors, which can deflect the measurement luminous flux in mutually different directions, are used as the optical scanner 46. However, another device that deflects the light (at least one of a polygon mirror, a resonant scanner, an acousto-optic device, and the like, for example) may be used as the optical scanner 46.

The lens 50 and the lens 52 are provided further to a downstream side (namely, the biological object side) on the optical path of the measurement luminous flux than the optical scanner 46. The lens 50 and the lens 52 function as a projection optical system that projects the measurement luminous flux toward the patient's eye E. The lenses 50 and 52 of the present embodiment are used in a Keplerian telescope. The OCT unit 40 includes an OCT focus adjustment unit 49 that adjusts the focus (hereinafter referred to as the "OCT focus") of the measurement optical system 43 that optically guides the measurement luminous flux. The OCT focus adjustment unit 49 illustrated in FIG. 2 includes the lens 50 of the front group of the Keplerian telescope, and an OCT focus adjustment motor 51. The OCT focus adjustment motor 51 can adjust the OCT focus by moving the lens 50 in a direction that is along the measurement luminous flux.

The reference optical system 54 optically guides the reference luminous flux and returns the reference luminous flux to the coupler 42. The reference optical system 54 of the present embodiment includes a collimator lens 55 and a reference mirror 57. The collimator lens 55 causes the reference luminous flux that has been split by the coupler 42 and has passed through a fiber to be a parallel luminous flux. The reference mirror 57 reflects the reference luminous flux and returns the reference luminous flux to the coupler 42. The configuration of the reference optical system 54 may be changed. For example, the reference optical system 54 may return the reference luminous flux that has been guided from the coupler 42 to the coupler 42 using a transmission type optical system, such as an optical fiber, without reflecting the reference luminous flux.

The OCT unit 40 includes an optical path length difference adjustment unit 56 that adjusts the optical path length difference between the measurement luminous flux and the reference luminous flux. By adjusting the optical path length difference, a range in a depth direction (the Z direction) over which the OCT signal is acquired is changed. The range in the depth direction over which the OCT signal is acquired is, for example, a field of view in the depth direction of the tomographic image, when the tomographic image is acquired. The optical path length difference adjustment unit 56 is provided on at least one of the optical path of the measurement luminous flux or the optical path of the reference luminous flux. The optical path length difference adjustment unit 56 illustrated in FIG. 2 includes the reference mirror 57 and an optical path length difference adjustment motor 58. The optical path length difference adjustment motor 58 adjusts the optical path length difference by moving the reference mirror 57 in a direction that is along the reference luminous flux. The configuration of the optical path length difference adjustment unit may be changed as appropriate. For example, the optical path length difference adjustment unit may adjust the optical path length difference by moving, in an optical axis direction, the collimator lens 44 provided on the optical path of the measurement luminous flux, and an end portion of the fiber that guides the measurement luminous flux from the coupler 42. Further, the optical path length difference adjustment unit may adjust the optical path length difference by moving, in the optical axis direction, the collimator lens 55 provided on the optical path of the reference luminous flux, and an end portion of the fiber that guides the reference luminous flux from the coupler 42.

The photodetection element 59 detects an interference state of the measurement luminous flux and the reference luminous flux. In the case of Fourier-domain OCT, the spectral intensity of an interference light is detected by the photodetection element 59, and a depth profile (an A scan signal) of a specified range is acquired by applying a Fourier transform to spectral intensity data. Various types of OCT may be used in the observation system 100. For example, any of spectral-domain OCT (SD-OCT), swept-source OCT (SS-OCT), time-domain OCT (TD-OCT), and the like may be adopted in the observation system 100.

Returning to the description of FIG. 1, the observation system 100 includes a line of sight direction detector 68 that detects a direction of a line of sight of the user. For example, a visible light camera is adopted as the line of sight direction detector 68 of the present embodiment. More specifically, the control unit 60 of the present embodiment processes an image of the eye of the user U captured by the line of sight direction detector 68, which is the visible light camera, and detects a positional relationship between the inner corner of the eye and the iris. The control unit 60 detects the direction of the line of sight of the user U on the basis of the positional relationship between the inner corner of the eye and the iris. However, the configuration of the line of sight direction detector 68 and the principle of detection may be changed. For example, an infrared camera may be used as the line of sight direction detector 68. In this case, the control unit 60 may process a captured image of the eye of the user U, and may detect the direction of the line of sight of the user U by detecting a positional relationship between the pupil and a corneal reflex bright spot.

Further, on the basis of the direction of the line of sight of the user U and information about a position of a display region on the display 67, the control unit 60 detects a position that is aligned with the direction of the line of sight of the user U in the display region. For example, in the present embodiment, the line of sight direction detector 68 is installed in a specified position in the display 67. However, the installation position of the line of sight direction detector 68 may be changed. For example, the line of sight direction detector 68 may be provided on a member worn by the user U (spectacles or the like causing the user U to stereoscopically view an image displayed on the display 67, for example).

The operation unit 69 may be operated by the user U to input various operation commands into the observation system 100. In this embodiment, a foot switch, which is operated by a foot of the user U, is at least provided as the operation unit 69. Therefore, the user can input various operation commands from the foot switch 69, while handling a surgical instrument with the user's hand. However, another device (various buttons or a touch panel, for example) may be used as the operation unit 69, together with the foot switch, or instead of the foot switch.

The control unit 60 controls various operations of the observation system 100 (such as adjustment control of the observation focus performed by the observation focus adjustment unit 32, and the like). The control unit 60 includes a CPU 61, a RAM 62, a ROM 63, and a non-volatile memory (NVM) 64. The CPU 61 is a controller that performs various types of control. The RAM 62 temporarily stores various kinds of information. The ROM 63 stores programs to be executed by the CPU 61, various initial values, and the like. The NVM 64 is a non-transitory storage medium capable of retaining stored content even when the supply of power is cut off. The NVM 64 may store an observation control program for executing observation focus automatic adjustment processing, which is described below.

In the present embodiment, as an example, the control unit 60 provided in the surgical microscope 1 functions as the control unit that performs the adjustment control of the observation focus and the like. Specifically, in the present embodiment, the surgical microscope 1 functions as the control device that controls the observation system 100. However, the configuration of the control unit that controls the observation system 100 (namely, the control unit that executes an observation control program) may be changed as appropriate. For example, a control unit of a personal computer (not shown in the drawings) connected to the surgical microscope 1 may control the observation system 100. Control units provided in each of a plurality of devices (the control unit 60 of the surgical microscope 1 and the control unit of the personal computer, for example) may operate in concert to control the observation system 100.

Acquiring Focus State of Observation Optical System

The control unit 60 of the present embodiment can acquire a focus state of the observation optical system 30 of the surgical microscope 1 (hereinafter sometimes simply referred to as an "observation focus state"). As will be described in detail below, as well as setting a target region inside the observation image in accordance with a detection result of the direction of the line of sight of the user U, the control unit 60 of the present embodiment can automatically adjust the focus of the target region in accordance with an acquisition result of the observation focus state (hereinafter, this adjustment is referred to as an "automatic focus adjustment"). Here, an example of a method of acquiring the observation focus state will be described. The control unit 60 of the present embodiment acquires the observation focus state on the basis of a signal from the imaging devices 36R and 36L. Thus, in the observation system 100 of the present embodiment, it is possible to omit a configuration dedicated to acquiring (detecting) the observation focus state.

As an example, the control unit 60 of the present embodiment acquires the observation focus state using a contrast detection method. More specifically, the control unit 60 analyzes the image in the target region of the observation image (a microscopic image in the present embodiment) captured by the imaging devices 36R and 36L, while changing the observation focus using the observation focus adjustment unit 32. The control unit 60 acquires the observation focus state by causing a position at which the contrast of the image in the target region is highest to be the position at which the observation focus is in focus. However, as described above, a method other than the contrast detection method may be used as the method for acquiring the observation focus state.

Modes

In the observation system 100 of the present embodiment, one of a plurality of modes relating to the focus adjustment of the observation image can be selected by the user. For example, in the present embodiment, three modes are provided, namely, a fully automatic mode (a constant execution mode), a semi-automatic mode (a signal input execution mode), and a stop mode. When the fully automatic mode is selected, the control unit 60 constantly or intermittently performs the automatic focus adjustment. When the semi-automatic mode is selected, the control unit 60 performs the automatic focus adjustment when triggered to do so by a trigger signal input by the user. When the stop mode is selected, the control unit 60 does not perform the automatic focus adjustment. Various methods may be adopted as the method that allows the user to select the mode. For example, one of the plurality of modes may be selected by the user operating one of a foot switch, an operating button, a touch panel, or the like.

In the present embodiment, the user can input the trigger signal in the semi-automatic mode by operating the operation unit 69. However, a method of inputting the trigger signal may be changed. For example, the observation system 100 may receive the input of the trigger signal by detecting voice generated by the user, or a gesture by the user. In this case, the user can input the trigger signal without touching a switch or the like with the user's hand. When detecting the gesture of the user, the detected gesture may be a gesture by a hand of the user, or may be a gesture by other than the hand (an inclination of the user's face or the like, for example).

Observation Focus Automatic Adjustment Processing

The observation focus automatic adjustment processing performed by the control unit of the observation system 100 (the control unit 60 of the surgical microscope 1 in the present embodiment) will be explained below. When the fully automatic mode or the semi-automatic mode is selected, the CPU 61 of the control unit 60 performs the observation focus automatic adjustment processing shown in FIG. 3, in accordance with an observation system control program stored in the NVM 64.

Figure 3:
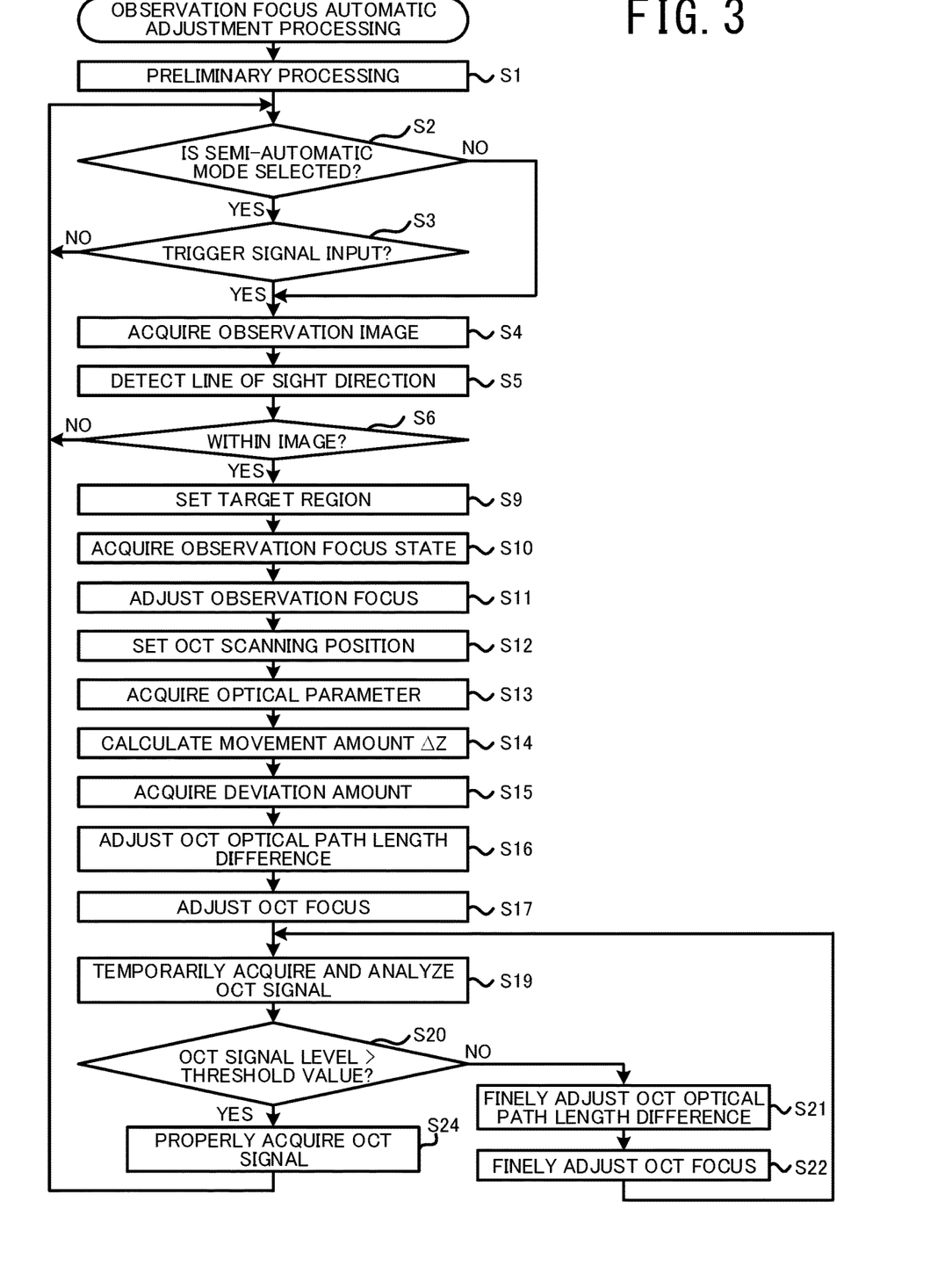
FIG. 3 is a flowchart showing an example of observation focus automatic adjustment processing.

First, the CPU 61 starts preliminary processing (S1). As described above, the CPU 61 captures an image of the patient's eye E using the imaging devices 36R and 36L of the observation optical system 30. In the preliminary processing, the CPU 61 starts display of the observation image, on the display 67, on the basis of imaging signals from the imaging devices 36R and 36L. In this case, the CPU 61 may acquire the observation focus state in a region set in advance (a region in the center of the image, for example) and may adjust the observation focus such that the observation focus state is favorable. Further, the CPU 61 may start the image capture and the display of the observation image by setting the observation focus at a midpoint of a range over which the observation focus can be adjusted, without acquiring the observation focus state. Further, the CPU 61 adjusts the optical path length difference in the OCT unit 40 on the basis of an optical parameter of the observation optical system 30. For example, a case is illustrated in which the objective lens 31 whose focal length can be changed is used and the focal length is changed from 170 mm to 200 mm. In this case, a distance from the objective lens 31 to the patient's eye E (a working distance) becomes approximately 30 mm longer. Thus, the CPU 61 controls the driving of the optical path length difference adjustment unit 56 on the basis of the optical parameter (the focal length) of the observation optical system 30, and causes the optical path length difference to change by approximately 30 mm.

Next, the CPU 61 performs processing depending on the selected mode (S2 and S3). When the fully automatic mode is selected (no at S2), the processing moves directly to S4, and the automatic focus adjustment (S4 to S11) is constantly performed. When the semi-automatic mode is selected (yes at S2), the CPU 61 determines whether the trigger signal has been input that is the trigger to perform the automatic focus adjustment (S3). When the trigger signal has not been input (no at S3), the processing returns to S2. When the trigger signal has been input (yes at S3), the processing moves to S4, and the automatic focus adjustment is performed.

In the automatic focus adjustment, the CPU 61 acquires data of the observation image captured by the imaging devices 36R and 36L (S4). The CPU 61 detects the direction of the line of sight of the user U using the line of sight direction detector 68 (S5). When the direction of the line of sight of the user U is not within the observation image displayed on a display region of the display 67 (no at S6), the processing returns directly to S2. When the direction of the line of sight of the user U is within the observation image (yes at S6), the CPU 61 sets the target region on the observation image in accordance with the direction of the line of sight of the user U (S9).

Figure 4:
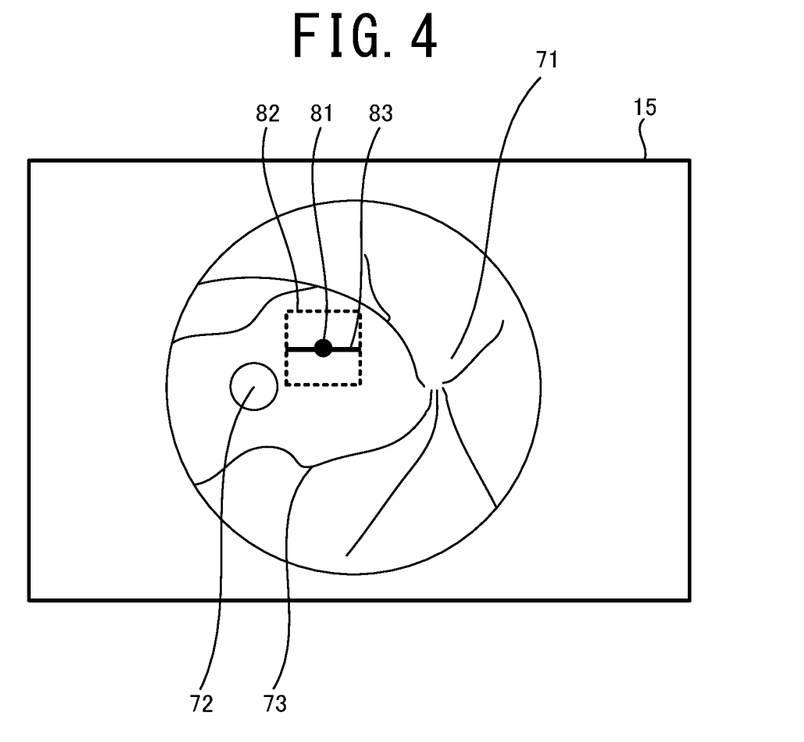
FIG. 4 is an explanatory diagram illustrating a target region 82 and a scanning position 83 set on an observation image 15.

An example of a method for setting a target region 82 in accordance with the direction of the line of sight will be explained with reference to FIG. 4. FIG. 4 illustrates observation image 15 when an image of the ocular fundus of the patient's eye E is captured. An optic papilla 71, a macula lutea 72, and a fundus oculi blood vessel 73 are pictured in the observation image 15. The CPU 61 of the present embodiment identifies, in the observation image 15, a position (hereinafter referred to as a line of sight position 81) with which the direction of the line of sight of the user is aligned. The CPU 61 sets the target region 82 to a region that includes the identified line of sight position 81. For example, the CPU 61 of the present embodiment sets the target region 82 on the observation image 15 such that the identified line of sight position 81 is at the center of the target region 82. Further, the CPU 61 of the present embodiment sets a size of the target region 82, in accordance with an operation command input by the user. Thus, the user can adjust the size of the target region 82 to a desired size. The size of the target region may be set in advance.

Next, the CPU 61 acquires the observation focus state (S10). As described above, the CPU 61 of the present embodiment acquires the observation focus state in the target region 82 on the basis of the signals from the imaging devices 36R and 36L inside the set target region 82.

Figure 5:
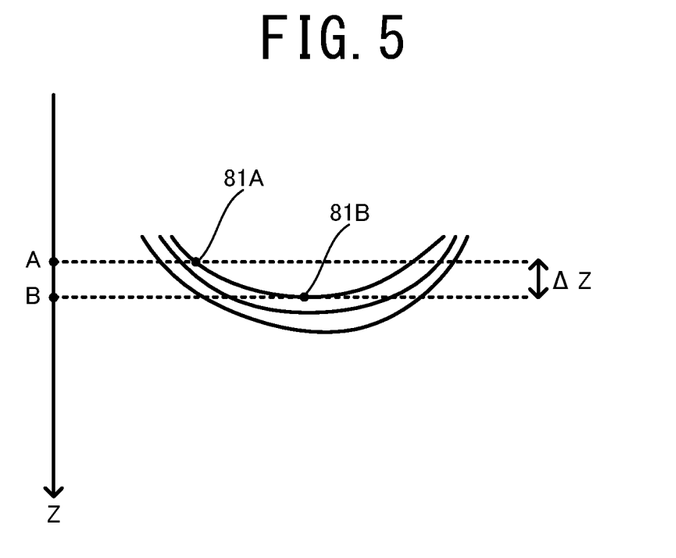
FIG. 5 is an explanatory diagram illustrating a state when a position of an observation focus changes in a depth direction, in accordance with a change in a position to be observed.

Next, by controlling the driving of the observation focus adjustment unit 32 on the basis of an acquisition result of the observation focus state, the CPU 61 adjusts the focus of the target region 82 in the observation image 15 (S11). In other words, the CPU 61 performs the automatic focusing on the basis of the direction of the line of sight of the user U. For example, in the example shown in FIG. 5, when the position of the line of sight of the user U moves from a position 81A to a position 81B on the ocular fundus, even if there is no movement of the patient's eye E, an appropriate position of the observation focus in the Z direction moves by ΔZ in a positive Z direction. In this case, the CPU 61 adjusts the focus of the target region 82 in the observation image 15 by controlling the driving of the observation focus adjustment unit 32 such that the observation focus state is focused in the target region 82. As a result, the focus of a position on which the user wishes to concentrate can be appropriately adjusted.

Further, in the processing at S11, the CPU 61 may adjust the focus on the basis of an offset amount input by the user. In the present embodiment, by operating the operation unit 69, the user may input the offset amount (a deviation amount), in a direction along the optical axis, of a desired focus position with respect to a normal focus position that is focused on the basis of the acquisition result of the observation focus state. The normal focus position that is focused on the basis of the acquisition result of the observation focus state is a focus position that is focused by the automatic focusing when the offset amount is "0". An input method of the offset amount may be selected as appropriate. For example, a method may be adopted in which the user is caused to select one option from "No offset," "Focal point of lens in front of the subject," and "Focal point of lens behind the subject." Taking "0" as the case in which there is no offset, a method may be adopted that causes the user to input a numerical value of a positive or negative deviation amount. When the offset amount is input, the CPU 61 may bring into focus a position that deviates by the input offset amount from the normal focus position that is based on the acquisition result of the observation focus state. In the present embodiment, the normal focus position that is based on the acquisition result of the observation focus state is the focus position at which the contrast of the target region 82 is most favorable.

Next, the CPU 61 performs OCT light adjustment processing (S12 to S24). First, on the basis of a detection result of the direction of the line of sight of the user U, the CPU 61 sets a scanning position 83 of the measurement luminous flux used to acquire the OCT signal (S12). In the example shown in FIG. 4, the CPU 61 sets the scanning position 83 such that the scanning position 83 passes through the detected line of sight position 81 and is contained within the target region 82. As a result of this, the tomographic image of the position on which the user U wishes to concentrate can be captured. A method for setting the scanning position 83 may be changed as appropriate. For example, the scanning position 83 may extend to the outside of the target region 82. A plurality of the scanning positions 83 may be set on the basis of the detection result of the direction of the line of sight.

Next, processing to adjust the OCT light in accordance with a change in the observation focus state in the target region 82 is performed (S13 to S17). As an example, on the basis of the optical parameter of the observation optical system 30 (including the observation focus adjustment unit 32) and a drive amount of the observation focus adjustment unit 32, the CPU 61 of the present embodiment calculates a movement amount $\Delta Z$ in the depth direction (the Z direction) of a position to be observed (a position on which the observation focus is focused). The CPU 61 adjusts the OCT light on the basis of the movement amount $\Delta Z$. This will be described in more detail below.

First, the CPU 61 acquires the optical parameter of the observation optical system 30 (S13). In the present embodiment, the focal length of the observation optical system 30 that is changed by the observation focus adjustment unit 32 is acquired. Further, in the present embodiment, the optical parameter changes depending on whether the wide angle observation unit 37 (see FIG. 1) is used. Thus, the CPU 61 of the present embodiment acquires the optical parameter in accordance with the presence or absence of the wide angle observation unit 37. Specifically, in the present embodiment, the CPU 61 acquires, as the optical parameters of the observation optical system 30, an image formation magnification $\beta_1$ and a longitudinal magnification $\alpha_1$ for the observation object in relation to an intermediate image of the observation optical system 30 (a front side focal position of the front lens 39), which change depending on whether the wide angle observation unit 37 is used and in accordance with the focal length). Further, in the present embodiment, the CPU 61 acquires a focal position of the lens 50 of the front group of the Keplerian telescope of the OCT unit 40 with respect to the observation object, namely, acquires an imaging magnification $\beta_2$ and a longitudinal magnification $\alpha_2$ for an intermediate image of an end face of the fiber.

Next, on the basis of the change in the observation focus state, the CPU 61 calculates the amount $\Delta Z$ by which the position to be observed has moved in the Z direction (S14). For example, in the example shown in FIG. 5, the observation focus is adjusted by the observation focus adjustment unit 32 as a result of the position to be observed moving from the position 81A to the position 81B. Thus, the CPU 61 can calculate the movement amount $\Delta Z$ of the position to be observed, from the drive amount of the observation focus adjustment unit 32. In the example shown in FIG. 1, if the movement amount of the observation focus with respect to a position of an intermediate image is denoted by $\Delta Z_1$, then $\Delta Z = \alpha_1 \times \Delta Z_1 = \beta_1^2 \times \Delta Z_1$ is obtained. In this case, the movement amount of the observation focus with respect to the position of the intermediate image matches an extending amount of the objective lens 31 and the reducing lens 38 of the observation focus adjustment unit 32.

Next, the CPU 61 acquires a deviation amount, in a depth direction (the Z direction) along the luminous flux, between the observation target position, which is the reference for focusing an observation focus Sf, and an OCT target position, which is a reference for acquiring the OCT signal (S15). The OCT target position is at least one of a target position that is a reference for focusing a zero delay position (a position at which the optical path length difference of the OCT light is zero), or a target position that is a reference for focusing an OCT focus Of. In the observation system 100 of the present embodiment, the user may independently specify the observation target position and the OCT target position in the depth direction by operating the operation portion 68. When the observation target position and the OCT target position are aligned in the depth direction, the deviation amount acquired at S15 is zero.

Next, by driving the optical path length difference adjustment unit 56 of the OCT unit 40 on the basis of the movement amount $\Delta Z$ in the Z direction of the position to be observed, the CPU 61 adjusts the optical path length difference (S16). In the present embodiment, the CPU 61 controls the driving of the optical path length difference adjustment motor 58 of the optical path length difference adjustment unit 56, and moves the reference mirror 57 by $\Delta Z \times n_g$, thus adjusting the optical path length difference. $n_g$ is a group index of the patient's eye E. For example, in the example shown in FIG. 5, as a result of the optical path length difference being adjusted in accordance with the change in the observation focus, an acquisition range of the OCT signal centered on a point A in the Z direction is changed to an acquisition range of the OCT signal centered on a point B. When there is the deviation between the observation target position and the target position for focusing the zero delay position, the CPU 61 drives the optical path length difference adjustment unit 56 while taking into account the deviation amount acquired at S15. Thus, even when there is deviation between the observation target position and the target position for focusing the zero delay position, the optical path length difference can be appropriately adjusted.

Next, by driving the OCT focus adjustment unit 49 on the basis of the movement amount $\Delta Z$ of the position to be observed, the CPU 61 adjusts the OCT focus (S17). In the present embodiment, as shown in FIG. 1, the measurement luminous flux of the OCT also passes through the observation focus adjustment unit 32. Thus, when the observation focus adjustment unit 32 is driven, the OCT focus also moves. However, due to a wavelength difference and the like between the observation light of the surgical microscope 1 and the OCT light, there is a case in which the movement amount of the observation focus and the movement amount of the OCT focus in relation to the drive amount of the observation focus adjustment unit 32 do not match each other. Thus, the CPU 61 of the present embodiment can more accurately adjust the OCT focus by also driving the OCT focus adjustment unit 49 in accordance with the change in the observation focus state.

The drive amount of the OCT focus adjustment unit 49 can be calculated on the basis of an optical parameter of the measurement optical system 43 and the like. As an example, if the movement amount of the OCT focus at the intermediate image position is denoted by $\Delta Z_2$, the image formation magnification of the measurement optical system 43 is denoted by $\beta_2$, the longitudinal magnification is denoted by $\alpha_2$, and the drive amount of the OCT focus adjustment unit 49 (the movement amount of the lens 52 in the present embodiment) is denoted by $\Delta Z_3$, then $\Delta Z_2 = \alpha_2 \times \Delta Z_3 = \beta_2 \times \Delta Z_3$ is obtained. $\Delta Z_2$ is determined in accordance with the movement amount $\Delta Z$ of the position to be observed that is calculated at S14, and thus, from the above-described formula, the drive amount of the OCT focus adjustment unit 49 can be calculated. When there is the deviation between the observation target position and the target position for focusing the OCT focus Of, the CPU 61 drives the OCT focus adjustment unit 49 while also taking into account the deviation amount acquired at S15.

By the processing from S13 to S17 being performed as described above, the adjustment of the OCT light is performed in accordance with the change in the observation focus state in the target region 82. As a result, the optical path length difference and the OCT focus of the OCT unit 40 can be rapidly and easily adjusted. Here, the OCT light may be adjusted only in accordance with the change in the observation focus state, but the CPU 61 of the present embodiment also adjusts the OCT light on the basis of an analysis result of the OCT signal (S19 to S22). As a result, the adjustment of the OCT light can be more appropriately adjusted. This will be described in detail below.

First, the CPU 61 temporarily acquires the OCT signal via the photodetection element 59 and analyzes the OCT signal (S19). Next, the CPU 61 determines whether the level of the analyzed OCT signal is greater than a threshold value (S20). When the level of the OCT signal is equal to or less than the threshold value (no at S20), the CPU 61 drives the optical path length difference adjustment unit 56 to finely adjust the optical path length difference (S21). Further, the CPU 61 drives the OCT focus adjustment unit 49 to finely adjust the OCT focus (S22). The processing returns to S19 and the processing from S19 to S22 is repeated until the level of the OCT signal is greater than the threshold value. The optical path length difference and the OCT focus are generally appropriately adjusted in accordance with the change in the observation focus state. Therefore, a range of the adjustment on the basis of the analysis result of the OCT signal (S19 to S22) can be made narrower. Thus, the OCT light can be rapidly and appropriately adjusted. When the level of the OCT signal becomes greater than the threshold value (yes at S20), the CPU 61 properly acquires the OCT signal (S24). The processing then returns to the determination at S2.

The method for analyzing the OCT signal may be selected as appropriate. For example, the CPU 61 may analyze signals for the whole of the acquired OCT image. Alternatively, of the acquired OCT image, the CPU 61 may analyze a signal for a specified range centered on the line of sight position 81. In this case, the quality of the OCT image in the range that includes the line of sight position 81 can be further improved. Of the acquired OCT image, the CPU 61 may carry out weighting such that the analysis result in the vicinity of the line of sight position 81 is accorded more significance than an analysis result of a position separated from the line of sight position 81.

The technology disclosed in the above-described embodiment may merely an example. Thus, the technology illustrated in the above-described embodiment may be modified.

For example, in the embodiment illustrated in FIG. 1 to FIG. 5, the target region 82 is set in accordance with the detection result of the direction of the line of sight of the user, and the focus is adjusted inside the set target region 82. However, the CPU 61 may set the target region 82 on the basis of information other than the direction of the line of sight of the user.

Figure 6:
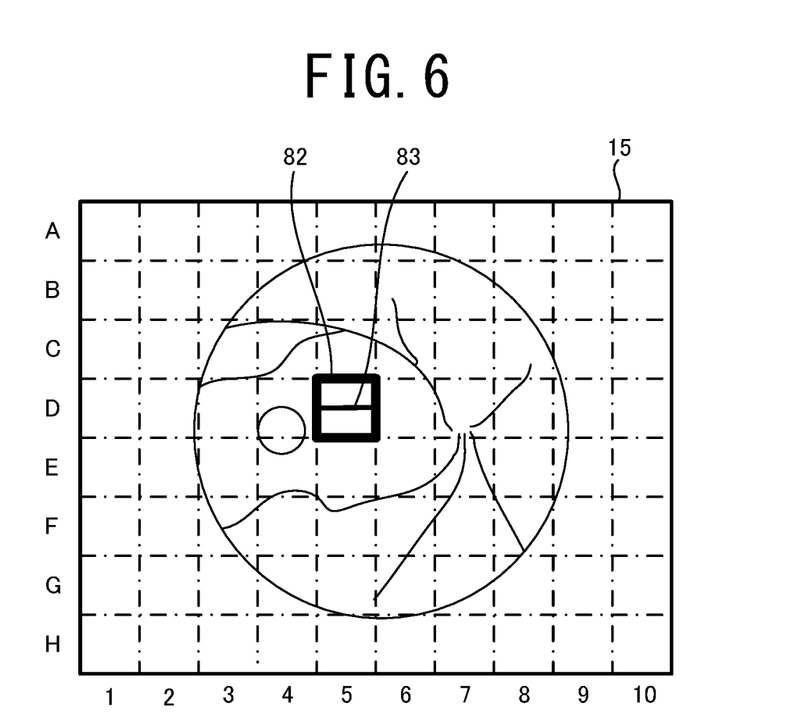
FIG. 6 is an explanatory diagram illustrating an example of a method for setting the target region 82 in accordance with voice generated by a user.

More specifically, the observation system 100 may be provided with a voice detector (a microphone, for example) that detects voice generated by the user. In this case, the CPU 61 may set the target region 82 in accordance with the voice detected by the voice detector. An example of a method for setting the target region 82 using the voice will be explained with reference to FIG. 6. In the example shown in FIG. 6, the observation image 15 displayed on the display 67 is divided into a plurality of regions. More specifically, in the example shown in FIG. 6, the observation image 15 is divided into eight sections A to H in the vertical direction, and into ten sections 1 to 10 in the horizontal direction. By voicing a block number in the vertical direction and the horizontal direction, the user may specify a position to be targeted. FIG. 6 shows a case in which the user has voiced "D5." The CPU 61 may set the target region 82 and the scanning position 83 to the block number specified by the voice of the user. However, the method for setting the target region 82 in accordance with the voice may be changed. For example, the user may specify the position to be targeted by voicing a direction in which the user wishes to move the target region 82 ("up," "right," and so on). In this case, the CPU 61 may move the target region 82 in the direction voiced by the user.

Further, the observation system 100 may be provided with a gesture detector that detects a gesture of the user. In this case, the CPU 61 may set the target region 82 in accordance with the gesture detected using the gesture detector. The gesture detector may be a camera, a sensor, or the like that detects the gesture of the user, for example. Further, the detected gesture may be a gesture of a hand or a foot of the user, for example, or may be a gesture using the face of the user (a tilt of the face and the like, for example).

In the embodiment illustrated in FIG. 1 to FIG. 5, the adjustment of the optical path length difference (S16) and the adjustment of the OCT focus (S17) are performed in accordance with the change in the observation focus state in the target region 82. As a result, the OCT focus can be rapidly and appropriately adjusted. However, in the example shown in FIG. 1, the OCT focus changes along with the observation focus by the driving of the observation focus adjustment unit 32. Therefore, in a case in which a difference between the movement amount of the observation focus and the movement amount of the OCT focus is small and the like when the observation focus adjustment unit 32 is driven, it is possible to perform the adjustment of the optical path length difference in accordance with the change in the observation focus state (S16), while omitting the drive processing of the OCT focus adjustment unit 49 in accordance with the change in the observation focus state (S17).

A determination may be made, on the basis of another condition, whether to perform the drive processing of the OCT focus adjustment unit 49 in accordance with the change in the observation focus state in the target region 82 (S17). For example, when using the OCT unit 40 to capture a tomographic image of an anterior ocular segment of the patient's eye E or the like, in order to prioritize deepening of the focal depth rather than enhancing the resolution, there may be a case in which the numerical aperture NA is made smaller by the NA adjustment unit 45. In contrast, in the case of capturing a tomographic image of the ocular fundus of the patient's eye E or the like, in order to prioritize the enhancing of the resolution, there may be a case in which the numerical aperture NA is made larger by the NA adjustment unit 45. When the numerical aperture NA is made larger, the focal depth becomes shallower and it is thus preferable for the OCT focus to be more accurately adjusted by the OCT focus adjustment unit 49. Therefore, the CPU 61 may determine, on the basis of the numerical aperture NA adjusted by the NA adjustment unit, whether to perform the drive processing of the OCT focus adjustment unit 49 in accordance with the change in the observation focus state (S17). For example, the CPU 61 may determine whether to perform the processing at S17 depending on whether the numerical aperture NA is equal to or greater than a threshold value.

The CPU 61 may omit the adjustment of the optical path length difference in accordance with the change in the observation focus state (S16) and may perform the drive processing of the OCT focus adjustment unit 49 in accordance with the change in the observation focus state (S17). In the above-described embodiment, the fine adjustment of the OCT optical path length difference (S21) and the fine adjustment of the OCT focus (S22) are both performed in accordance with the analysis result of the OCT signal. However, the processing at least one of S21 or S22 may be omitted.

In the embodiment exemplified in FIG. 1 to FIG. 5, the adjustment of the OCT light is automatically performed in accordance with the change in the observation focus state in the target region 82. However, the adjustment of the OCT light (the setting of the scanning position 83, or the adjustment of the optical path length difference, or the like, for example) need not necessarily be performed in concert with the change in the observation focus state in the target region 82. In this case, the processing from S12 to S24 shown in FIG. 3 is omitted. Further, this also applies to the case in which the observation system 100 does not include the OCT unit 40.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. An observation system comprising:
an observation optical system guiding an observation luminous flux from a biological object being an observation target observed by a user;
an imaging device capturing an observation image of the biological object, by receiving the observation luminous flux guided by the observation optical system;
an observation focus adjustment unit provided on an optical path of the observation luminous flux in the observation optical system, the observation focus adjustment unit adjusting a focus of the observation optical system;
a detector detecting at least one of a direction of a line of sight of the user, voice generated by the user, or a gesture of the user; and
a processor controlling an operation of the observation system,
wherein
the processor
causes the observation image captured by the imaging device to be displayed on a display,
adjusts a focus of a target region concentrated on by the user in the observation image, by driving the observation focus adjustment unit based on a detection result by the detector,
sets the target region on the observation image captured by the imaging device, based on the detection result by the detector,
acquires a focus state of the observation optical system,
adjusts the focus of the target region in the observation image, by driving the observation focus adjustment unit based on an acquisition result of the focus state of the observation optical system,
receives a selection command to select one of a plurality of modes including an execution mode and a stop mode, the execution mode being a mode in which automatic focus adjustment of the target region is performed based on the acquisition result of the focus state of the observation optical system, and the stop mode being a mode in which the automatic focus adjustment is stopped, and
controls an operation of the automatic focus adjustment in accordance with the selected mode.

2. The observation system according to claim 1, wherein
the observation optical system guides an observation luminous flux for a right eye and an observation luminous flux for a left eye from the biological object to the imaging device, and
the processor causes a stereoscopic image to be displayed on the display, based on an imaging signal for the right eye and an imaging signal for the left eye that are issued by the imaging device.

3. The observation system according to claim 1, wherein
the detector includes a camera and detects the gesture by a face of the user.

4. The observation system according to claim 1, wherein
the detector includes a line of sight direction detector, the line of sight direction detector detecting the direction of the line of sight of the user, and
the processor sets the target region to a region, of the observation image captured by the imaging device and displayed on the display, that is positioned in the direction of the line of sight detected by the line of sight direction detector.

5. The observation system according to claim 1, wherein
the execution mode includes a signal input execution mode, the signal input execution mode being a mode in which the automatic focus adjustment is performed when a trigger signal is input, and
when the signal input execution mode is selected, by using an input of the trigger signal as a trigger, the processor sets the target region based on the detection result by the detector and adjusts the focus of the target region based on the acquisition result of the focus state of the observation optical system.

6. The observation system according to claim 1, wherein
the execution mode includes a constant execution mode, the constant execution mode being a mode in which the automatic focus adjustment is constantly performed, and when the constant execution mode is selected, the processor constantly or intermittently performs setting the target region and adjusting the focus of the target region.

7. The observation system according to claim 1, wherein the processor acquires the focus state of the observation optical system based on a signal inside the set target region, of signals from the imaging device.

8. The observation system according to claim 1, wherein the processor
receives an input of an offset amount of a focus position desired by the user, with respect to a focus position being based on the acquisition result of the focus state of the observation optical system, and
brings into focus a position deviated, by the input offset amount, from the focus position being based on the acquisition result of the focus state of the observation optical system.

9. The observation system according to claim 1, further comprising:
an OCT unit acquiring an OCT signal,
wherein
the OCT unit includes:
an OCT light source;
a light splitter splitting a luminous flux emitted from the OCT light source into a measurement luminous flux and a reference luminous flux;
a photodetection element receiving interference light obtained by synthesizing the reference luminous flux and the measurement luminous flux reflected by the biological object; and
an optical path length difference adjustment unit provided on at least one of an optical path of the measurement luminous flux or an optical path of the reference luminous flux, the optical path length difference adjustment unit adjusting an optical path length difference between the measurement luminous flux and the reference luminous flux,
the processor
sets a position at which the OCT unit causes the measurement luminous flux to perform scanning, based on the detection result by the detector, and
drives the optical path length difference adjustment unit in the OCT unit in accordance with a change in a focus state of the target region.

10. A non-transitory computer-readable medium storing computer-readable instructions that, when executed by a processor of a control unit controlling an observation system, cause the control unit to perform processes comprising:
causing an observation image captured by an imaging device to be displayed on a display, the observation system comprising an observation optical system and the imaging device, the observation optical system guiding an observation luminous flux from a biological object, and the imaging device capturing the observation image of the biological object, by receiving the observation luminous flux guided by the observation optical system;
adjusting a focus of a target region concentrated on by a user in the observation image, by driving an observation focus adjustment unit based on a detection result by a detector, the observation system further comprising the observation focus adjustment unit and the detector, the observation focus adjustment unit being provided on an optical path of the observation luminous flux in the observation optical system, the observation focus adjustment unit adjusting a focus of the observation optical system, and the detector detecting at least one of a direction of a line of sight of the user, voice generated by the user, or a gesture of the user;
setting the target region on the observation image captured by the imaging device, based on the detection result by the detector;
acquiring a focus state of the observation optical system;
adjusting the focus of the target region in the observation image, by driving the observation focus adjustment unit based on an acquisition result of the focus state of the observation optical system;
receiving a selection command to select one of a plurality of modes including an execution mode and a stop mode, the execution mode being a mode in which automatic focus adjustment of the target region is performed based on the acquisition result of the focus state of the observation optical system, and the stop mode being a mode in which the automatic focus adjustment is stopped; and
controlling an operation of the automatic focus adjustment in accordance with the selected mode.

* * * * *